US012686703B2

(12) United States Patent
Mondon et al.

(10) Patent No.: US 12,686,703 B2
(45) Date of Patent: Jul. 21, 2026

(54) COSMETIC TETRAPEPTIDE, COMPOSITION AND USE

(71) Applicant: Sederma, Le Perray-en-Yvelines (FR)

(72) Inventors: Philippe Mondon, Montrouge (FR); Olivier Peschard, Rambouillet (FR); Richard Leroux, Faverolles (FR)

(73) Assignee: Sederma, Le Perray-en-Yvelines (FR)

( * ) Notice: Subject to any disclaimer, the term of this patent is extended or adjusted under 35 U.S.C. 154(b) by 525 days.

(21) Appl. No.: 18/035,855

(22) PCT Filed: Nov. 15, 2021

(86) PCT No.: PCT/EP2021/081729
§ 371 (c)(1),
(2) Date: May 8, 2023

(87) PCT Pub. No.: WO2022/106366
PCT Pub. Date: May 27, 2022

(65) Prior Publication Data
US 2024/0010677 A1 Jan. 11, 2024

(30) Foreign Application Priority Data
Nov. 17, 2020 (FR) ...................................... 2011745

(51) Int. Cl.
| | |
|---|---|
| *C07K 5/103* | (2006.01) |
| *A61K 8/49* | (2006.01) |
| *A61K 8/60* | (2006.01) |
| *A61K 8/64* | (2006.01) |
| *A61K 8/73* | (2006.01) |
| *A61K 8/9789* | (2017.01) |
| *A61K 38/00* | (2006.01) |
| *A61P 17/14* | (2006.01) |
| *A61Q 7/00* | (2006.01) |
| *A61Q 19/00* | (2006.01) |
| *A61Q 19/08* | (2006.01) |

(52) U.S. Cl.
CPC ............ *C07K 5/101* (2013.01); *A61K 8/4913* (2013.01); *A61K 8/498* (2013.01); *A61K 8/602* (2013.01); *A61K 8/64* (2013.01); *A61K 8/735* (2013.01); *A61K 8/9789* (2017.08); *A61P 17/14* (2018.01); *A61Q 7/00* (2013.01); *A61Q 19/00* (2013.01); *A61Q 19/08* (2013.01); *A61K 38/00* (2013.01)

(58) Field of Classification Search
CPC .... C07K 5/101; A61K 8/9789; A61K 8/4913; A61K 8/498; A61K 8/602; A61K 8/64; A61K 8/735; A61P 17/14; A61Q 7/00; A61Q 19/00; A16Q 19/08
See application file for complete search history.

(56) References Cited

U.S. PATENT DOCUMENTS

2008/0044857 A1* 2/2008 Anderson .......... C12N 15/1065
435/71.1

FOREIGN PATENT DOCUMENTS

| | | |
|---|---|---|
| KR | 20150111148 A | 10/2015 |
| WO | 2011026039 A1 | 3/2011 |
| WO | 2014080376 A2 | 5/2014 |
| WO | 2015181688 A1 | 12/2015 |
| WO | 2016097965 A1 | 6/2016 |
| WO | 2017216177 A1 | 12/2017 |

OTHER PUBLICATIONS

International Search Report and Written Opinion for International Application No. PCT/EP2021/081729, dated Feb. 22, 2022, 9 pages.

* cited by examiner

*Primary Examiner* — Li N Komatsu
(74) *Attorney, Agent, or Firm* — Buchanan Ingersoll & Rooney PC

(57) ABSTRACT

The tetrapeptide has the general Formula X-LLAN-Z (SEQ ID NO: 6) wherein at the N-terminal end X is selected from H, —CO—$R^1$, —$SO_2$—$R^1$ or a biotinoyl group, at the C-terminal end Z is selected from OH, $OR^1$, $NH_2$, $NHR^1$ or $NR^1R^2$, and $R^1$ and $R^2$ are selected from an alkyl, aryl, aralkyl, alkylaryl, alkoxy, saccharide and aryloxy, said group having from 1 to 24 carbon atoms. A preferred peptide is the Pal-LLAN-OH (SEQ ID NO: 7). This tetrapeptide can stimulate the synthesis of molecules constituting the dermal extracellular matrix, in particular collagen 1 and fibrillin 1, and can be used for a cosmetic treatment, in particular anti-aging, anti wrinkle and fine lines, to improve the skin mechanical properties, firmness/tone/elasticity/flexibility, to increase skin density and volume, for a restructuring effect and/or to fight against stretch marks, and skin sagging. The peptide is also adapted to stimulate hair growth.

16 Claims, No Drawings

Specification includes a Sequence Listing.

SEQUENCE LISTING

```
<160> NUMBER OF SEQ ID NOS: 31

<210> SEQ ID NO 1
<211> LENGTH: 5
<212> TYPE: PRT
<213> ORGANISM: artificial sequence
<220> FEATURE:
<223> OTHER INFORMATION: synthetic peptide
<220> FEATURE:
<221> NAME/KEY: MOD_RES
<222> LOCATION: (1)..(1)
<223> OTHER INFORMATION: amidation by a Palmitoyl chain on the N
      terminal end

<400> SEQUENCE: 1

Lys Thr Thr Lys Ser
1               5

<210> SEQ ID NO 2
<211> LENGTH: 4
<212> TYPE: PRT
<213> ORGANISM: artificial sequence
<220> FEATURE:
<223> OTHER INFORMATION: synthetic peptide
<220> FEATURE:
<221> NAME/KEY: MOD_RES
```

```
<222> LOCATION: (1)..(1)
<223> OTHER INFORMATION: amidation by a Palmitoyl chain on the N
      terminal end

<400> SEQUENCE: 2

Gly Gln Pro Arg
1

<210> SEQ ID NO 3
<211> LENGTH: 6
<212> TYPE: PRT
<213> ORGANISM: artificial sequence
<220> FEATURE:
<223> OTHER INFORMATION: synthetic peptide
<220> FEATURE:
<221> NAME/KEY: MOD_RES
<222> LOCATION: (1)..(1)
<223> OTHER INFORMATION: amidation by a Palmitoyl chain on the N
      terminal end

<400> SEQUENCE: 3

Val Gly Val Ala Pro Gly
1               5

<210> SEQ ID NO 4
<211> LENGTH: 5
<212> TYPE: PRT
<213> ORGANISM: artificial sequence
<220> FEATURE:
<223> OTHER INFORMATION: synthetic peptide

<400> SEQUENCE: 4

Lys Thr Thr Lys Ser
1               5

<210> SEQ ID NO 5
<211> LENGTH: 6
<212> TYPE: PRT
<213> ORGANISM: artificial sequence
<220> FEATURE:
<223> OTHER INFORMATION: synthetic peptide

<400> SEQUENCE: 5

Val Gly Val Ala Pro Gly
1               5

<210> SEQ ID NO 6
<211> LENGTH: 4
<212> TYPE: PRT
<213> ORGANISM: artificial sequence
<220> FEATURE:
<223> OTHER INFORMATION: synthetic peptide
<220> FEATURE:
<221> NAME/KEY: MOD_RES
<222> LOCATION: (1)..(1)
<223> OTHER INFORMATION: the amino acid is either unmodified or modified
      by acylation -CO-R1, or -SO2-R1 or by a biotinoyl, R1 = a 1 to
      24C, alkyl, aryl, aralkyl, alkylaryl, alkoxy, saccharide or
      aryloxy group
<220> FEATURE:
<221> NAME/KEY: MOD_RES
<222> LOCATION: (4)..(4)
<223> OTHER INFORMATION: the amino acid is either unmodified or modified
      in OR1, NH2, NHR1 or NR1R2, R1 and R2 = a 1 to 24C, alkyl, aryl,
      aralkyl, alkylaryl, alkoxy, saccharide or aryloxy group, R1 and R2
      being chosen independently

<400> SEQUENCE: 6

Leu Leu Ala Asn
1
```

```
<210> SEQ ID NO 7
<211> LENGTH: 4
<212> TYPE: PRT
<213> ORGANISM: artificial sequence
<220> FEATURE:
<223> OTHER INFORMATION: synthetic peptide
<220> FEATURE:
<221> NAME/KEY: MOD_RES
<222> LOCATION: (1)..(1)
<223> OTHER INFORMATION: amidation by a Palmitoyl chain on the N
      terminal end

<400> SEQUENCE: 7

Leu Leu Ala Asn
1

<210> SEQ ID NO 8
<211> LENGTH: 4
<212> TYPE: PRT
<213> ORGANISM: artificial sequence
<220> FEATURE:
<223> OTHER INFORMATION: synthetic peptide

<400> SEQUENCE: 8

Arg Ser Arg Lys
1

<210> SEQ ID NO 9
<211> LENGTH: 4
<212> TYPE: PRT
<213> ORGANISM: artificial sequence
<220> FEATURE:
<223> OTHER INFORMATION: synthetic peptide

<400> SEQUENCE: 9

Gly Gln Pro Arg
1

<210> SEQ ID NO 10
<211> LENGTH: 4
<212> TYPE: PRT
<213> ORGANISM: artificial sequence
<220> FEATURE:
<223> OTHER INFORMATION: synthetic peptide

<400> SEQUENCE: 10

Lys Thr Phe Lys
1

<210> SEQ ID NO 11
<211> LENGTH: 4
<212> TYPE: PRT
<213> ORGANISM: Artificial sequence
<220> FEATURE:
<223> OTHER INFORMATION: Synthetic peptide

<400> SEQUENCE: 11

Lys Thr Ala Lys
1

<210> SEQ ID NO 12
<211> LENGTH: 4
<212> TYPE: PRT
<213> ORGANISM: Artificial sequence
<220> FEATURE:
<223> OTHER INFORMATION: Synthetic peptide
```

```
<400> SEQUENCE: 12

Lys Ala Tyr Lys
1

<210> SEQ ID NO 13
<211> LENGTH: 4
<212> TYPE: PRT
<213> ORGANISM: Artificial sequence
<220> FEATURE:
<223> OTHER INFORMATION: Synthetic peptide

<400> SEQUENCE: 13

Lys Phe Tyr Lys
1

<210> SEQ ID NO 14
<211> LENGTH: 5
<212> TYPE: PRT
<213> ORGANISM: artificial sequence
<220> FEATURE:
<223> OTHER INFORMATION: synthetic peptide

<400> SEQUENCE: 14

Lys Thr Ser Lys Ser
1               5

<210> SEQ ID NO 15
<211> LENGTH: 5
<212> TYPE: PRT
<213> ORGANISM: artificial sequence
<220> FEATURE:
<223> OTHER INFORMATION: synthetic peptide
<220> FEATURE:
<221> NAME/KEY: MISC_FEATURE
<222> LOCATION: (5)..(5)
<223> OTHER INFORMATION: Xaa being either a Proline or a Leucine

<400> SEQUENCE: 15

Tyr Gly Gly Phe Xaa
1               5

<210> SEQ ID NO 16
<211> LENGTH: 6
<212> TYPE: PRT
<213> ORGANISM: artificial sequence
<220> FEATURE:
<223> OTHER INFORMATION: synthetic peptide

<400> SEQUENCE: 16

Gly Lys Thr Thr Lys Ser
1               5

<210> SEQ ID NO 17
<211> LENGTH: 6
<212> TYPE: PRT
<213> ORGANISM: artificial sequence
<220> FEATURE:
<223> OTHER INFORMATION: synthetic peptide
<220> FEATURE:
<221> NAME/KEY: MISC_FEATURE
<222> LOCATION: (6)..(6)
<223> OTHER INFORMATION: Xaa being Trp, Phe, Tyr, Tic, 7-hydroxy-Tic or
      Tpi

<400> SEQUENCE: 17

His Leu Asp Ile Ile Xaa
1               5
```

```
<210> SEQ ID NO 18
<211> LENGTH: 4
<212> TYPE: PRT
<213> ORGANISM: artificial sequence
<220> FEATURE:
<223> OTHER INFORMATION: synthetic peptide
<220> FEATURE:
<221> NAME/KEY: MOD_RES
<222> LOCATION: (1)..(1)
<223> OTHER INFORMATION: amidation by a Elaidoyl chain on the N terminal
      end

<400> SEQUENCE: 18

Lys Thr Phe Lys
1

<210> SEQ ID NO 19
<211> LENGTH: 4
<212> TYPE: PRT
<213> ORGANISM: Artificial sequence
<220> FEATURE:
<223> OTHER INFORMATION: Synthetic peptide
<220> FEATURE:
<221> NAME/KEY: MOD_RES
<222> LOCATION: (1)..(1)
<223> OTHER INFORMATION: amidation by a Elaidoyl chain on the N terminal
      end

<400> SEQUENCE: 19

Lys Thr Ala Lys
1

<210> SEQ ID NO 20
<211> LENGTH: 4
<212> TYPE: PRT
<213> ORGANISM: Artificial sequence
<220> FEATURE:
<223> OTHER INFORMATION: Synthetic peptide
<220> FEATURE:
<221> NAME/KEY: MOD_RES
<222> LOCATION: (1)..(1)
<223> OTHER INFORMATION: amidation by a Elaidoyl chain on the N terminal
      end

<400> SEQUENCE: 20

Lys Ala Tyr Lys
1

<210> SEQ ID NO 21
<211> LENGTH: 4
<212> TYPE: PRT
<213> ORGANISM: Artificial sequence
<220> FEATURE:
<223> OTHER INFORMATION: Synthetic peptide
<220> FEATURE:
<221> NAME/KEY: MOD_RES
<222> LOCATION: (1)..(1)
<223> OTHER INFORMATION: amidation by a Elaidoyl chain on the N terminal
      end

<400> SEQUENCE: 21

Lys Phe Tyr Lys
1

<210> SEQ ID NO 22
<211> LENGTH: 4
<212> TYPE: PRT
<213> ORGANISM: Artificial sequence
<220> FEATURE:
<223> OTHER INFORMATION: Synthetic peptide
```

```
<220> FEATURE:
<221> NAME/KEY: MOD_RES
<222> LOCATION: (1)..(1)
<223> OTHER INFORMATION: amidation by a Palmitoyl chain on the N
      terminal end

<400> SEQUENCE: 22

Lys Thr Phe Lys
1

<210> SEQ ID NO 23
<211> LENGTH: 5
<212> TYPE: PRT
<213> ORGANISM: artificial sequence
<220> FEATURE:
<223> OTHER INFORMATION: synthetic peptide
<220> FEATURE:
<221> NAME/KEY: MOD_RES
<222> LOCATION: (1)..(1)
<223> OTHER INFORMATION: amidation by a Palmitoyl chain on the N
      terminal end

<400> SEQUENCE: 23

Lys Thr Ser Lys Ser
1               5

<210> SEQ ID NO 24
<211> LENGTH: 5
<212> TYPE: PRT
<213> ORGANISM: artificial sequence
<220> FEATURE:
<223> OTHER INFORMATION: synthetic peptide
<220> FEATURE:
<221> NAME/KEY: MOD_RES
<222> LOCATION: (1)..(1)
<223> OTHER INFORMATION: amidation by a Palmitoyl chain on the N
      terminal end
<220> FEATURE:
<221> NAME/KEY: MISC_FEATURE
<222> LOCATION: (5)..(5)
<223> OTHER INFORMATION: Xaa being either a Proline P or a Leucine L.

<400> SEQUENCE: 24

Tyr Gly Gly Phe Xaa
1               5

<210> SEQ ID NO 25
<211> LENGTH: 6
<212> TYPE: PRT
<213> ORGANISM: artificial sequence
<220> FEATURE:
<223> OTHER INFORMATION: synthetic peptide
<220> FEATURE:
<221> NAME/KEY: MOD_RES
<222> LOCATION: (1)..(1)
<223> OTHER INFORMATION: amidation by a Palmitoyl chain on the N
      terminal end

<400> SEQUENCE: 25

Gly Lys Thr Thr Lys Ser
1               5

<210> SEQ ID NO 26
<211> LENGTH: 6
<212> TYPE: PRT
<213> ORGANISM: Artificial sequence
<220> FEATURE:
<223> OTHER INFORMATION: Synthetic peptide
<220> FEATURE:
<221> NAME/KEY: MOD_RES
<222> LOCATION: (1)..(1)
```

```
<223> OTHER INFORMATION: amidation by a Palmitoyl chain on the N
      terminal end
<220> FEATURE:
<221> NAME/KEY: MISC_FEATURE
<222> LOCATION: (6)..(6)
<223> OTHER INFORMATION: Xaa being Trp, Phe, Tyr, Tic, 7-hydroxy-Tic or
      Tpi

<400> SEQUENCE: 26

His Leu Asp Ile Ile Xaa
1               5

<210> SEQ ID NO 27
<211> LENGTH: 6
<212> TYPE: PRT
<213> ORGANISM: artificial sequence
<220> FEATURE:
<223> OTHER INFORMATION: synthetic peptide
<220> FEATURE:
<221> NAME/KEY: MOD_RES
<222> LOCATION: (1)..(1)
<223> OTHER INFORMATION: Acetylation on the N-terminal end

<400> SEQUENCE: 27

Glu Glu Met Gln Arg Arg
1               5

<210> SEQ ID NO 28
<211> LENGTH: 5
<212> TYPE: PRT
<213> ORGANISM: artificial sequence
<220> FEATURE:
<223> OTHER INFORMATION: synthetic peptide

<400> SEQUENCE: 28

Tyr Ala Gly Phe Leu
1               5

<210> SEQ ID NO 29
<211> LENGTH: 4
<212> TYPE: PRT
<213> ORGANISM: artificial sequence
<220> FEATURE:
<223> OTHER INFORMATION: synthetic peptide

<400> SEQUENCE: 29

Ala His Ser His
1

<210> SEQ ID NO 30
<211> LENGTH: 6
<212> TYPE: PRT
<213> ORGANISM: artificial sequence
<220> FEATURE:
<223> OTHER INFORMATION: synthetic peptide

<400> SEQUENCE: 30

Ser Ile Lys Val Ala Val
1               5

<210> SEQ ID NO 31
<211> LENGTH: 6
<212> TYPE: PRT
<213> ORGANISM: artificial sequence
```

-continued

```
<220> FEATURE:
<223> OTHER INFORMATION: synthetic peptide

<400> SEQUENCE: 31

Gly Pro Gln Gly Pro Gln
1               5
```

COSMETIC TETRAPEPTIDE, COMPOSITION AND USE

CROSS-REFERENCE TO RELATED APPLICATIONS

This application is the U.S. National Phase of PCT/EP2021/081729, filed Nov. 15, 2021, which claims the benefit of French Application No. 2011745, filed Nov. 17, 2020, each of which is incorporated by reference herein in its entirety for all purposes.

TECHNICAL FIELD

The present invention relates to a novel tetrapeptide, a composition comprising it, and its use in cosmetics. It concerns more particularly tetrapeptides adapted for the treatment of skin and its integuments (such as hair, eyelashes, eyebrows, nails) of mammals, animals or humans. It concerns the (topical or oral) cosmetics, hygiene and personal care products and dermo-pharmacy industries.

BACKGROUND ART

Peptides have an important signaling function and coordinate many biochemical processes in the body. They have therefore become essential and promising active ingredients, more particularly in the cosmetic industry where new compounds capable of embellishing the skin and its integuments are constantly being sought, that is to improve their general condition.

The present inventors were more particularly interested in finding new peptides having an activity on molecules constituting the dermal extracellular matrix (ECM) which decrease with age, such as collagen I and fibronectin.

Thanks to the stimulated synthesis of ECM molecules by fibroblasts, the dermal cells in charge of their production, results on beautifying skin and improving its general condition are obtained, in particular regarding the mechanical properties: a denser, plumped, firmer, more toned, more supple and elastic skin is obtained, the peptide having a volumizing, plumping, and therefore anti-wrinkle effect. Results are also obtained at the level of complexion imperfections (skin color is more homogeneous and radiance is improved).

Numerous peptides or mixtures of anti-aging peptides have been already proposed, capable of stimulating the synthesis of collagen I, in particular by the Applicant, such as the Pal-KTTKS (SEQ ID NO: 1), marketed under the trademark MATRIXYL®, the Pal-GHK, the Pal-GQPR (SEQ ID NO: 2), a mixture of these two peptides marketed under the trademark MATRIXYL® 3000, the Pal-KMO$_2$K under the trademark MATRIXYL® SYNTHE'6® (MO$_2$ corresponding to a dioxygenated methionine) or more recently the Pal-K(P)HG (with a proline grafted onto the lysine) marketed under the trademark MATRIXYL® MORPHOMICS®. Other peptides have been proposed in cosmetics for their specific ability to stimulate elastin synthesis, such as the Ac-YR-hexadecyl ester, marketed by the Applicant under the trademark IDEALIFT™, or the Pal-VGVAPG (SEQ ID NO: 3), marketed under the trademark DERMAXYL™ by the Applicant.

The peptidic sequences may correspond or approximate fragments of ECM constituent molecules. For example, the KTTKS peptide sequence (SEQ ID NO: 4) corresponds to a fragment of collagen and the VGVAPG sequence (SEQ ID NO: 5) to a fragment of elastin. The term "matrikines" is used for those peptides which by mimicry stimulate cell activity and the synthesis of corresponding macromolecules.

The aim of the present invention is to provide a further peptide which can improve the general condition of the skin and of their integuments, and more particularly a peptide which are active on the synthesis of ECM proteins. In addition, the invention aims to provide a peptide that is sufficiently effective that can be used alone or in combination, be active from a few ppm, and in the form of topical composition, in particular a cosmetic composition.

The present invention provides a tetrapeptide of Formula 1:

X-LLAN-Z (SEQ ID NO: 6)

wherein:
at the N-terminal X chosen from H, —CO—R$^1$, —SO$_2$—R$^1$ or a biotinoyl group,
at the C-terminal Z end chosen from OH, OR$^1$, NH$_2$, NHR$^1$ or NR$^1$R$^2$, and
R$^1$ and R$^2$ being, independently of each other, chosen from an alkyl, aryl, aralkyl, alkylaryl, alkoxy, saccharide and aryloxy group, which may be linear, branched, cyclic, polycyclic, unsaturated, hydroxylated, carbonylated, phosphorylated and/or sulfured, said group having from 1 to 24 carbon atoms and optionally having in its backbone one or more heteroatoms O, S and/or N.

As commonly used, in the LLAN peptidic sequence: the amino acid L corresponds to a Leucine (Leu), the amino acid A corresponds to an Alanine (Ala) and the amino acid N corresponds to an Asparagine (Asp).

This peptidic sequence corresponds to a fragment of a dermal ECM macromolecule, Emilin 1, which is a glycoprotein located at the level of the sites where elastin and microfibrils are found nearby.

At the N-terminal end, when X=H, it means that the terminal amino acid L is not modified. At the C-terminal end, when Z=OH, it means that the terminal amino acid N is not modified. When X=H and Z=OH, the tetrapeptide according to the invention is thus in a non-derivatised form. The aim of a derivatisation of the tetrapeptide in N and/or C terminal end is, in particular, to improve the biodisponibility of the peptide by enhancing skin penetration. This role can also be obtained by vectorisation of the peptide(s), through encapsulation for example.

The detailed description of in-vitro tests given below shows that the tetrapeptide of the invention advantageously exhibit activity on important ECM molecules, are active from a few ppm, and can be used to improve the appearance and general condition of skin and its integuments, and in particular for the treatment and/or prevention of signs of aging, and/or imperfections of the skin, and of its integuments.

The inventors have shown that surprisingly the tetrapeptide according to the invention can stimulate the synthesis of collagen I and fibrillin 1.

Fibrillin 1 is a connective tissue protein produced by fibroblasts and smooth muscle cells that helps forming extracellular microfibrils. The fibrillin-containing microfibrils interact with both basement membranes and neighboring elastic fibers and can help to stabilize the extracellular matrix by forming a scaffold.

The inventors have also shown that surprisingly the tetrapeptide according to the invention is adapted for a hair treatment, more particularly to stimulate hair growth.

According to other preferred features of the invention:

the tetrapeptide according to the invention is modified at its N-terminal and/or C-terminal end;

preferably modified only at its N-terminal end; and/or $R^1$ and/or $R^2$ is an alkyl chain of 1 to 24 carbon atoms, preferably a lipophilic alkyl chain of 3 to 24 carbon atoms; and/or X is a acyl group CO—$R^1$ and Z is selected from OH, OMe, OEt and $NH_2$, preferably OH; X is preferably selected from octanoyl (C8), decanoyl (C10), lauroyl (C12), myristoyl (C14), palmitoyl (C16), stearoyl (C18), biotinoyl, elaidoyl, oleoyl and lipoyl; more preferably selected from a lauroyl (C12), myristoyl (C14) and palmitoyl (C16); and/or Z is OH and X is selected from palmitoyl (C16), myristoyl (C14) and lauroyl (C12); more preferably palmitoyl (C16).

Tetrapeptides comprising at the N or C terminal ends derivatives of particular acids such as those of ascorbic, retinoic, cinnamic, oleanolic, hyaluronic, nicotinic, lipoic, gallic or pantothenic acid are also included in the present invention.

The particularly preferred tetrapeptide of the invention is the Pal-LLAN-OH (SEQ ID NO: 7).

The tetrapeptides according to the invention can be optically pure or consist of the L or D isomers or a mixture thereof. L isomers which are those naturally occurring may be preferred.

The present invention also includes derivatives (with modification and/or addition of a chemical function to one or more of the amino acids but without change in the carbon skeleton) and the analogs (with modification and/or addition of a chemical function to one or more of the amino acids but with in addition a change in the carbon skeleton), and complexes with other species such as a metal ion (eg copper, zinc, manganese, magnesium, and others).

The tetrapeptides can optionally be in the form of salts, in particular hydrochloric salt, or acetate.

The active peptide sequence according to the invention LLAN can also form part of a peptide having additional amino acids on either side of this sequences.

The present invention also provides a composition, in particular topical, comprising the tetrapeptide according to the invention and a physiologically acceptable medium. Depending on the physiologically acceptable medium and the dosage of tetrapeptide, this composition may constitute a concentrated active ingredient intended to enter into a final composition for a consumer, or may directly constitute said final composition, which is less concentrated.

In a composition according to the invention, the least one tetrapeptide may be present at a higher or lower concentration depending on its destination, ranging from 10-7% to 20% relative to the total weight of the composition, preferably ranging from 10-6% to 10%, more preferably from $10^{-5}$% to 5%, by weight relative to the total weight of the composition.

For example, in a composition forming an active ingredient, the at least one tetrapeptide will be present at a higher concentration generally ranging from 0.001% to 1% (10 ppm to 10,000 ppm), preferably ranging from 0.01% to 0.15% (100 ppm to 1500 ppm). This ingredient will then generally be formulated between 1 and 10%.

All the percentages and ratios used in the present application are expressed relative to the weight of the total composition and all the measurements are made at 25° C. unless otherwise specified.

By "physiologically acceptable medium" is meant according to the present invention, without limitation, an aqueous or hydroalcoholic solution, a water-in-oil emulsion, an oil-in-water emulsion, a microemulsion, an aqueous gel, an anhydrous gel, a serum, a vesicle dispersion, or a powder.

"Physiologically acceptable" means that the compositions are suitable for topical or transdermal use, in contact with the mucous membranes, nails, scalp, hair, body hair and skin of mammals and more particularly of humans, compositions which can be ingested or injected into the skin, without risk of toxicity, incompatibility, instability, allergic response, and others. This "physiologically acceptable medium" forms what is conventionally called the excipient of the composition.

The tetrapeptide according to the invention can be solubilized in a lipophilic or hydrophilic matrix, optionally with a solubilizer, depending on the intended application.

The peptide(s) in the treatment according to the invention can be combined with other active ingredients at effective concentrations which can act synergistically or in reinforcement to achieve the desired effects described for the invention, such as the following agents: anti-aging, anti-wrinkles and fine lines, brightening, pro-pigmenting, moisturizing, humectant, slimming, anti-acne, anti-inflammatory, antioxidant, acting on the radiance of the complexion, anti-glycation, volumizing, restructuring, anti-carbonylation, dermorelaxants, anti-hair growth, acting on the stratum corneum, on the dermis-epidermis junction, on the production of HSPs proteins, on the firmness, elasticity, skin tone, hair growth (eyelashes, eyebrows for example), etc.

These active ingredients can be obtained from plant materials, such as plant extracts or products of in-vitro plant culture or fermentation.

More specifically, the tetrapeptide(s) can be combined with at least one of the compounds selected from vitamin B3 compounds, compounds such as niacinamide or tocopherol, retinoid compounds such as retinol, hexamidine, α-lipoic acid, resveratrol or DHEA, hyaluronic acid, peptides, in particular Ac-YR-hexadecyl ester (also called N-acetyl-Tyr-Arg-O-hexadecyl ester), Pal-VGVAPG (SEQ ID NO: 3), Pal-KTTKS (SEQ ID NO: 1), Pal-GHK, Pal-KMO$_2$K, Pal-GQPR (SEQ ID NO: 2), and Pal-K(P)HG, which are known active ingredients used in topical cosmetic or dermo-pharmaceutical compositions.

More preferably, the tetrapeptide(s) according to the invention are associated to the peptides Ac-YR-hexadecyl ester, Pal-GHK and/or Pal-GQPR (SEQ ID NO: 2).

Other compounds which can advantageously be combined with the tetrapeptides according to the invention are mentioned below in the detailed description, and in particular in the galenical part.

The composition according to the invention can be applied to the face, the body, the neckline, the scalp, the hair, the eyelashes, the body hairs, in any form or vehicle known to those skilled in the art, in particular in the form of a solution, dispersion, emulsion, paste or powder, individually or as a premix or be conveyed individually or as a premix by vectors such as macrocapsules, microcapsules or nanocapsules, macrospheres, microspheres, or nanospheres, liposomes, oleosomes or chylomicrons, macroparticles, microparticles or nanoparticles, macro-sponges, micro-sponges or nano-sponges, microemulsions or nanoemulsions, or adsorbed on powdery organic polymers, tales, bentonites, spores or exines and other mineral or organic supports.

In cosmetics, applications can be proposed for example in the ranges of skin care for face, body, hair (including eyelashes, eyebrows and body hair) and ranges of make-up treatments.

Generally, the peptides according to the present invention can be used in any form, in a linked form, incorporated or adsorbed on macro-, micro-, and nano-particles, or on macro-, micro- and nano-capsules, for the treatment of textiles, natural or synthetic fibers, wool, and all materials intended to come into contact with the skin or hair and which can be used in clothing, day or night underwear, handkerchiefs, or fabrics, in order to exercise its cosmetic or therapeutic (dermatological) effect through this skin or hair/ textile contact and allow continuous topical delivery.

The CTFA ("International Cosmetic Ingredient Dictionary & Handbook" published by "The Cosmetic, Toiletry, and Fragrance Association, Inc.", Washington, DC) describes a wide variety, without limitation, of cosmetic ingredients usually used in the skincare industry, which are suitable for use as additional ingredients in compositions according to the present invention.

Other additional skin care actives that are particularly useful can be found in Sederma's commercial literature and at <www.croda.com>.

The following marketed active ingredients can also be mentioned as examples: betain, glycerol, ACTIMOIST BIO 2™ (Active organics), AQUACACTEEN™ (Mibelle AG Cosmetics), AQUAPHYLINE™ (Silab), AQUAREG-ULK™ (Solabia), CARCILINE™ (Greentech), CODIAVE-LANE™ (Biotech Marine), DERMAFLUX™ (Arch Chemicals, Inc), HYDRA'FLOW™ (Sochibo), HYDRO-MOIST L™ (Symrise), RENOVHYAL™ (Soliance), SEA-MOSS™ (Biotech Marine), ARGIRELINE™ (commercial name of acetyl hexapeptide-3 from Lipotec), spilanthol or an extract of *Acmella oleracea* known under the trade name GATULINE EXPRESSION™, an extract of Boswellia *serrata* known under the name BOSWELLIN™, DEEPALINE PVB™ (Seppic), SYN-AKE™ (Pentapharm), AME-LIOX™, BIOXILIFT™ (Silab), PHYTOCELLTEC™ Argan (Mibelle), PAPILACTYL D™ (Silab), PREVEN-THELIA™ (Lipotec), or one or more of the following cosmetic active ingredients marketed by Sederma: SUB-LISKIN™, VENUCEANE™, MOIST 24™, VEGESOME MOIST 24™, ESSENSKIN™, JUVINITY™, REVID-RAT™, RESISTEM™, CHRONODYN™, KOMBU-CHKA™, CHROMOCARE™, CALMOSENSINE™, GLYCOKIN FACTOR S™, BIOBUSTYL™, IDEA-LIFT™, CERAMIDE 2™, CERAMIDE A2™, CER-AMIDE HO3™, LEGANCE™, INTENSLIM™, PRODI-ZIA™, BEAUTIFEYE™, PACIFEEL™, ZINGERSLIM™, MEIRITAGE™, SENESTEM™, SEBULESS™, MAJESTEM™, APISCALP™, RUBISTEM™, CIT-YSTEM™. NEONYCA™, NG UNSAPONIFIABLE SHEA BUTTER™, MAJESTEM™, HYDRONESIST™, PORETECT™, CRYSTALIDE™, AMBERSTEM™, SYN-CHROLIFE™, FEMINAGE™, AMEYEZING™, or mixtures thereof.

More preferably, a composition according to the invention comprises at least one the following active ingredient IDEA-LIFT™ (based on the peptide Ac-YR-hexadecyl ester) and/ or MATRIXYL®3000 (based on a mixture of the Pal-GHK and Pal-GQPR peptides), preferably Idealift™ and MATRIXYL®3000.

Among plant extracts (in the form of classical plant extracts or prepared by an in-vitro process) that can be combined with the peptide(s) according to the present invention, there may more particularly be mentioned extracts of Ivy, in particular English Ivy (*Hedera helix*), of *Bupleurum chinensis*, of *Bupleurum falcatum*, of arnica (*Arnica montana* L), of rosemary (*Rosmarinus officinalis* N), of marigold (*Calendula officinalis*), of sage (*Salvia officinalis* L), of ginseng (*Panax ginseng*), of *Ginko biloba*, of St.-John's-Wort (*Hyperycum perforatum*), of butcher's-broom (*Ruscus aculeatus* L), of European meadowsweet (*Filipendula ulmaria* L), of big-flowered Jarva tea (*Orthosiphon stamincus benth*), of artichoke (*Cynara scolymus*), of algae (*Fucus vesiculosus*), of birch (*Betula alba*), of green tea, of cola nuts (s), of horse-chestnut, of bamboo, of *Centella asiatica*, of heather, of *Fucus*, of willow, of mouse-ear, of escine, of cangzhu, of *Chrysanthellum indicum*, of the plants of the *Armeniacea* genus, *Atractylodis platicodon, Sinnomenum, Pharbitidis, Flemingia*, of *Coleus* such as *C. Forskohlii, C. blumei, C. esquirolii, C. scutellaroides, C. xanthantus* and *C. Barbatus*, such as the extract of root of *Coleus barbatus*, extracts of *Ballote*, of *Guioa*, of *Davallia*, of *Terminalia*, of *Barringtonia*, of *Trema*, of *Antirobia, Cecropia, Argania, Dioscoreae* such as *Dioscorea opposita* or Mexican, extracts of *Ammi visnaga*, of *Siegesbeckia*, in particular *Siegesbeckia orientalis*, vegetable extracts of the family of Ericaceae, in particular bilberry extracts (*Vaccinium angustifollium*) or *Arctostaphylos uva ursi*, aloe vera, plant containing sterols (e.g., phytosterol), Manjistha (extracted from plants of the genus *Rubia*, particularly *Rubia cordifolia*), and Guggal (extracted from plants of the genus *Commiphora*, particularly *Commiphora mukul*), kola extract, chamomile, red clover extract, *Piper methysticum* extract (Kava Kava™ from Sederma), *Bacopa monieri* extract (Bacocalmine™ from Sederma) and sea whip extract, extracts of *Glycyrrhiza glabra*, of mulberry, of *Melaleuca* (tea tree), of *Larrea divaricata*, of *Rabdosia rubescens*, of *Euglena gracilis*, of *Fibraurea recisa hirudinea*, of *Chaparral sorghum*, of sun flower extract, of *Enantia chlorantha*, of Mitracarpe of *Spermacocea* genus, of *Buchu barosma*, of *Lawsonia inermis* L., of *Adiantium capillus-veneris* L., of *Chelidonium majus*, of *Luffa cylindrica*, of Japanese Mandarin (*Citrus reticulata* Blanco var. *unshiu*), of *Camelia sinensis*, of *Imperata cylindrica*, of *Glaucium flavum*, of *Cupressus sempervirens*, of *Polygonatum multiflorum*, of *Loveyly hemsleya*, of *Sambucus nigra*, of *Phaseolus lunatus*, of *Centaurium*, of *Macrocystis pyrifera*, of *Turnera diffusa*, of *Anemarrhena asphodeloides*, of *Portulaca pilosa*, of *Humulus lupulus*, of *Coffea arabica*, of *Ilex paraguariensis*, or of *Globularia cordifolia*, of *Albizzia julibrissin*, of *Oxydendron arboretum*, of *Zingimber zerumbet* smith, of *Astragalus membranaceus*, of *Atractylodes macrocephalae*, of *Plantago lanceolata*, of *Leontopodium alpinum*, of *Mirabilis jalapa*, of *Marrubium vulgare*, of *Apium graveolens*, of *Marrubium vulgare*, of *Buddleja davidii* Franch, *Engelhardia chrysolepis, Syringa vulgaris* or of orchids.

The compositions of the present invention may include other additional peptides, including, without limitation, di-, tri-, tetra-, penta- and hexapeptides and their derivatives. According to a particular embodiment, the concentration of the additional peptide, in the composition, ranges from $1 \times 10^{-7}\%$ and 20%, preferably from $1 \times 10^{-6}\%$ and 10%, preferably between $1 \times 10^{-5}\%$ and 5% by weight. The term "peptide" refers here to peptides containing 10 amino acids or less, their derivatives, isomers and complexes with other species such as a metal ion (e.g. copper, zinc, manganese, magnesium, and others). The term "peptides" refers to both natural peptides and synthetic peptides. It also refers to compositions that contain peptides and which are found in nature, and/or are commercially available.

Suitable dipeptides for use herein include but are not limited to Carnosine (βAH), YR, VW, NF, DF, KT, KC, CK, KP, KK, TT, PA, PM or PP.

Suitable tripeptides for use herein include, but are not limited to RKR, HGG, GKH, GHK, GGH, GHG, KGH, KHG, KFK, KAvaK, KβAK, KAbuK, KAcaK, KPK, KMOK, KMO$_2$K (MO$_2$ being a dioxygenated sulfoxide methionine), KVK, PPL, PPR, SPR, QPA, LPA, SPA, K(Ac) HG or K(Ac)GH, K(Ac) being a lysine with the amine function of the lateral chain acetylated, as disclosed in WO2017/216177, K(P)HG or K(P)GH, K(P) being a lysine with its lateral chain grafted with a proline, K(Pyr)HG or K(Pyr)GH, K(Pyr) being a lysine with its lateral chain grafted with a pyroglutamic acid, K(Hyp)HG or K(Hyp)GH, K(Hyp) being a lysine with its lateral chain grafted with a hydroxyproline, as disclosed in WO2016/097965.

Suitable tetrapeptides for use as additional peptides herein include but are not limited to RSRK (SEQ ID NO: 8), GQPR (SEQ ID NO: 9), KTFK (SEQ ID NO: 10), KTAK (SEQ ID NO: 11), KAYK (SEQ ID NO: 12) or KFYK (SEQ ID NO: 13).

Suitable non limitative examples of pentapeptide are the KTTKS (SEQ ID NO: 4), the KTSKS (SEQ ID NO: 14) and the YGGFXaa (SEQ ID NO: 15) with Xaa being Leu or Pro, and of hexapeptides the GKTTKS (SEQ ID NO: 16), VGVAPG (SEQ ID NO: 5) and HLDIIXaa with Xaa being Trp, Phe, Tyr, Tic, 7-hydroxy-Tic or Tpi (SEQ ID NO: 17).

Other suitable peptides for use according to the present invention can be selected, this list being not limitative, from: lipophilic derivatives of peptides, preferably palmitoyl (Pal) derivatives or myristoyl (Myr), and metal complexes as aforementioned (e.g. copper complex of the tripeptide HGG or GHK).

Preferred dipeptides include for example N-Palmitoyl-β-Ala-His, N-Acetyl-Tyr-Arg-hexadecylester (CALMO-SENSINE™, IDEALIFT™ from Sederma), Pal-RT or Pal-KT (from Sederma). Preferred tripeptide derivatives include for example Pal-GKH and Pal-GHK (from Sederma), the copper derivative of HGG (LAMIN™ from Sigma), Lipospondin (N-Elaidoyl-KFK) and its analogs of conservative substitution, N-Acetyl-RKR-NH2 (Peptide CK+), N-Biot-GHK (from Sederma), Pal-KAvaK, Pal-KβAlaK, Pal-KA-buK, Pal-KAcaK, or Pal-KMO2K (MATRIXYL®SYNTHE'6® from Sederma), Pal-KVK (Syn-Coll™ of DSM), Pal-K(P)HG (MATRIXYL® MORPHOMICS® from Sederma) and derivatives thereof.

Mention may also be made here of the anti-aging tripeptides of general Formula X-Pro*-Pro*-Xaa-Y described in WO2015181688 application with Xaa selected from Leu, Arg, Lys, Ala, Ser, and Asp, at the N-terminus, X chosen from H, —CO—R1 and —SO2-R1 and at the C-terminal end Y chosen from OH, OR1, NH2, NHR1 or NR1R2, R1 and R2 being, independently of one another, chosen from a alkyl, aryl, aralkyl, alkylaryl, alkoxy and aryloxy group, which may be linear, branched, cyclic, polycyclic, unsaturated, hydroxylated, carbonylated, phosphorylated and/or sulfurized, said group possibly possessing in its backbone a heteroatom particularly O, S and/or or N, and Pro* corresponding to Proline, an analogue or derivative thereof, comprising, for example, Myr-PPL-OH and Myr-PPR-OH.

Here can further be cited also the propigmenting and/or pro-mec dipeptides and tripeptides of general Formula X-(Xaa1)n-Pro*-Xaa2-Y disclosed in WO2014/080376, with n=0, 1 or 2, Xaa1 an hydrophobic aminoacid selected from Ala, Val, Met, Leu, Iso, Phe, Pro, and analogs and derivatives thereof, or a polar aminoacid selected from Ser, Thr, Tyr, Asp, Glu and analogs and derivatives thereof; and when n=2 the two aminoacids Xaa1 being the same or different; Xaa2 being an hydrophobic aminoacid selected from Ala, Val, Met, Leu, Iso, Phe, and analogs and derivatives thereof, or a basic aminoacid selected from Arg, Lys, His, and analogs and derivatives thereof, at the N terminal end X being selected from H, —CO—R1 and —SO2-R1; at the C terminal end Y being selected from OH, OR1, NH2, NHR1 or NR1R2; R1 and R2 being, independently from each other, selected from an alkyl, aryl, aralkyl, alkylaryl, alkoxy et aryloxy group, that can be linear, branched, cyclic polycyclic, saturated, unsaturated, hydroxylated, carbonylated, phosphorylated and/or sulfured, said group having or not an O, S and/or N heteroatom in its skeleton and Pro* corresponding to a Proline, analog or derivative thereof, comprising for example the following peptides Pal-SPR-OH, Pal-PPR-OH, Pal-QPA-OH, Pal-LPAOH, Myr-SPA-OH, Pal-PM-OH, Pal-PA-OH and Pal-PP-OH.

Suitable tetrapeptide derivatives for use as additional peptides according to the present invention include, but are not limited to, Pal-GQPR (SEQ ID NO: 2) (from Sederma), Ela-KTFK (SEQ ID NO: 18), Ela-KTAK (SEQ ID NO: 19), Ela-KAYK (SEQ ID NO: 20), Ela-KFYK (SEQ ID NO: 21) or Pal-KTFK (SEQ ID NO: 22). Suitable pentapeptide derivatives for use as additional peptides herein include, without being limited to, Pal-KTTKS (SEQ ID NO: 1) (available as MATRIXYL® from Sederma), the Pal-KTSKS (SEQ ID NO: 23), Pal-YGGFXaa (SEQ ID NO: 24) with Xaa being Leu or Pro, or mixtures thereof.

Suitable hexapeptide derivatives for use herein include, but are not limited to, Pal-VGVAPG (SEQ ID NO: 3), Pal-GKTTKS (SEQ ID NO: 25), Pal-HLDIIXaa with Xaa being Trp, Phe, Tyr, Tic, 7-hydroxy-Tic ou Tpi (SEQ ID NO: 26) and derivatives thereof. The mixture of Pal-GHK and Pal-GQPR (SEQ ID NO: 2) (MATRIXYL®3000, Sederma) can also be mentioned.

The preferred compositions commercially available containing a tripeptide or a derivative include BIOPEPTIDE-CL™, MAXILIP™, BIOBUSTYL™, PROCAPIL™, MATRIXYL® SYNTHE'6® or MATRIXYL® MORPHOMICS® of Sederma. The compositions commercially available preferred sources of tetrapeptides include RIGIN™, EYELISS™, MATRIXYL® Reloaded and MATRIXYL 3000® which contain between 50 and 500 ppm of Pal-GQPR (SEQ ID NO: 2) and an excipient, proposed by Sederma.

The following marketed peptides can be mentioned as well as additional active ingredients:

VIALOX™ (INCI name=Pentapeptide-3 (synthetic peptide comprising alanine, arginine, isoleucine, glycine and proline)), Syn-ake™ (β-Ala-Pro-Dab-NH-Bzl) or Syn-Coll™ (Pal-Lys-Val-Lys-OH) sold by Pentapharm;

ARGIRELINE™ (Ac-Glu-Glu-Met-Gln-Arg-Arg-NH$_2$ (INCI name=Acetyl hexapeptide-3) (SEQ ID NO: 27), LEUPHASYL™ (Tyr-D-Ala-Gly-Phe-Leu) (SEQ ID NO: 28), ALDENINE™ (Gly-His-Lys), TRY-LAGEN™ (INCI name=*Pseudoalteromonas* Ferment Extract, Hydro lyzed Wheat Protein, Hydro lyzed Soy Protein, Tripeptide-10 Citrulline (reaction product of Citrulline and Tripeptide-10 (synthetic peptide constituted of aspartic acid, isoleucine and lysine)), Tripeptide-1), EYESERYL™ (Ac-p-Ala-His-Ser-His)(SEQ ID NO: 29), SERILESINE™ (Ser-Ile-Lys-Val-Ala-Val) (SEQ ID NO: 30) or DECORINYL™ (INCI name: Tripeptide-10 Citrulline=reaction product of Citrulline and Tripeptide-10 (synthetic peptide constituted of aspartic acid, isoleucine and lysine) sold by Lipotec;

COLLAXYL™ (Gly-Pro-Gln-Gly-Pro-Gln (SEQ ID NO: 31)) or QUINTESCINE™ (Cys-Gly) sold by Vincience;

CYTOKINOL™ LS (casein hydrolysate) sold by Les Laboratoires Serobiologiques/Cognis;

KOLLAREN™ (Gly-His-Lys), IP2000™ (Pal-Val-Tyr-Val) or MELIPRENE™ (INCI name=Monofluoroheptapeptide-1: reaction product of acetic acid and a synthetic peptide comprising arginine, glycine, glutamic acid, histidine, norleucine, p-fluoro-phenylalanine and tryptophan) sold by l'Institut Européen de Biologie Cellulaire;

NEUTRAZEN™ (Pal-His-D-Phe-Arg-NH₂) sold by Innovations; or

BONT-L-PEPTIDE™ (INCI name=Palmitoyl Hexapeptide-19: reaction product of palmitic acid and Hexapeptide-19 (synthetic peptide constituted of asparagine, aspartic acid, lysine and methionine), TIMP-PEPTIDE™ (INCI name=Acetyl Hexapeptide-20: reaction product obtained by acetylation of Hexapeptide-20 (synthetic peptide constituted of alanine, glycine, lysine, valine and proline) or ECM MODULINE™ (INCI name=Palmitoyl Tripeptide-28: reaction product of palmitic acid and Tripeptide-28 (synthetic peptide constituted of arginine, lysine and phenylalanine) sold by Infinitec Activos.

The present invention thus provides the use of a tetrapeptide according to the invention or of a composition comprising it, as defined above, for a non-therapeutic cosmetic treatment to improve the general condition of the skin and/or its appendages and treat imperfections. The treatment consists of applying an effective amount of a tetrapeptide according to the invention to skin and/or its appendages in need thereof.

According to the invention, the treatment is preferably a topical treatment.

The tetrapeptide according to the invention is more particularly adapted according to the invention for an anti-aging treatment (as a preventive and/or curative), in particular a treatment:

anti-wrinkles and fine lines; and/or improving the mechanical properties of the skin: firmness, tone, elasticity and/or flexibility; and/or increasing the density and volume of the skin (volumizing, plumping and/or restructuring effect); and/or to fight against stretch marks; and/or to fight against skin sagging; and/or to improve the uniformity and/or radiance of the complexion.

Other applications can be considered for the tetrapeptide according to the invention, for example moisturizing, slimming, detoxification, anti-glycation, anti-free radicals, tensors, anti-fatigue, anti-puffiness and/or dark circles, soothing/calming, action on hair growth, on pigmentation, on the scalp, etc. as a preventive or curative treatments.

In vitro-tests detailed below show in particular that the peptide according to the invention can stimulate hair growth.

The tetrapeptide according to the invention is therefore furthermore more particularly adapted for a hair growth stimulation treatment.

The present invention provides a cosmetic, non-therapeutic topical treatment method for improving the appearance and general condition of the skin and its integuments, comprising topical application to the skin of a subject in need thereof of an effective amount of a peptide according to the invention, or of a composition according to the invention comprising said peptide, the peptide being as defined above.

A "non-therapeutic cosmetic treatment" means a treatment which is intended for skin and its integuments being in a healthy state (as opposed to a pathological state), with the aim of beautifying it or avoiding disorders (as a preventive measure), in particular aesthetic or sensory disorders.

By "topical treatment" or "topical use" is meant an application which is intended to act at the place where it is applied: skin, mucous membrane, integuments.

The peptide or composition according to the invention can be applied locally to targeted areas.

The "effective" amount depends on various factors, such as age, the cutaneous state of the user, the intensity of the disorder and the mode of administration. An effective amount means a non-toxic amount sufficient to achieve the desired effect, in particular a more or less pronounced effect.

For example, for a cosmetic facial treatment, the European Cosmetics Directive has set a standard application amount of a cream of 2.72 $mg/cm^2$/day/person and for a body lotion of 0.5 $mg/cm^2$/day/person.

According to other features, the cosmetic treatment method according to the invention can be associated with one or more other treatment methods aimed at the skin, such as, for example, light therapy, heat, vibration, electroporation treatments, micro-needle patch, or aromatherapy.

According to the invention, devices can be proposed with several compartments or kits intended for the implementation of the method described above, and which could include, by way of example, and without being limiting, in a first compartment a composition comprising a tetrapeptide according to the invention and in a second compartment an excipient and/or additional active, the compositions contained in said first and second compartments being here considered as a combination composition for simultaneous, separate or spread over time use especially in one of the treatments defined above.

The treatment method according to the invention is more particularly suitable for slowing down the degradation of molecules of the dermal extracellular matrix.

According to yet another object, the present invention provides the use of a tetrapeptide according to the invention as an active ingredient in the preparation of a cosmetic composition for improving the general condition of the skin and/or its appendages and to treat their imperfections.

DETAILED DESCRIPTION

The present invention will be better understood in the light of the following description of an embodiment and of in-vitro tests.

A—Example of Synthesis of a Tetrapeptide According to the Invention: The Pal-LLAN-OH (SEQ ID NO: 7)

The Pal-LLAN-OH (SEQ ID NO: 7) is prepared by peptidic synthesis. The N-protected asparagine is attached to a resin via its terminal acid function. The amine function is deprotected and then the asparagine-resin is reacted with an alanine derivative in the presence of a coupling agent (for example DCC (dicyclohexylcarbodiimide)/NHS (N-hydroxysuccinimide) or HBTU (2-(1H-benzotriazole)-1-yl)-1,1,3,3-tetramethyluronium hexafluorophosphate)/HOBT (1-hydroxy-benzotriazole), then the same deprotection and coupling operations are repeated to add a first leucine, a second leucine and palmitic acid. The peptide is then cleaved from the resin in an acidic medium and after precipitation, washing and drying, the product palmitoyl-leucyl-leucyl-alanyl-asparagine is obtained in solid form.

The tetrapeptides according to the invention can also be prepared biotechnologically, via a microorganism capable of at least partially producing it.

B—Example of Preparation of a Composition According to the Invention Comprising the Tetrapeptide Pal-LLAN-OH (SEQ ID NO: 7) of Example A Starting Materials:

the pure peptide, synthesized according to the synthesis process explained above.

excipient: mixture of fatty esters, chosen to form an oily matrix, for example intended to form an anhydrous composition for the subsequent formulation of anhydrous cosmetic compositions.

Protocol: a selected amount of one of the two peptides is mixed with the excipient and placed under gentle stirring and heating until solubilization and complete clarity.

In a particular example 1200 ppm of one of the peptide Pal-LLAN-OH (SEQ ID NO: 7) of the invention is mixed with the excipient to form an active ingredient used in the below galenic part D).

C—In-Vitro Evaluations

The tetrapeptide according to the invention exhibit remarkable effects presented below. The tetrapeptide prepared according to A) above and dissolved in an excipient was tested in-vitro and showed activities which are presented below.

1—Stimulation of MEC Proteins 1.1—ELISA Assays

Protocol

Normal human fibroblasts (NHF) in culture are brought into contact with the products to be tested or their excipient (negative control) for 72 h. At the end of the contact, the culture supernatants are removed, and the syntheses of the dermal macromolecules are estimated by ELISA assays. An estimate of cell viability is carried out by Hoechst assay to weight the obtained data.

Collagen I is evaluated via the PIP assay (carboxy-terminal propeptide of procollagen type I) which is a peptide fragment resulting from the enzymatic degradation of pro-collagen when the latter is excreted outside the fibroblast (therefore in the culture medium where the assay is carried out).

Results

TABLE 1

| | Pal-LLAN-OH (SEQ ID NO: 7) (Concentrations of 5 to 15 ppm) | Significance |
| --- | --- | --- |
| Collagen I (PIP) | +60% | p < 0.01 |

1.2—Immunofluorescence Assays

Protocol

Normal human fibroblasts (NHF) are cultured for at least 24 hours in fibroblast growth medium containing serum. Once confluence was reached, the cells are seeded, and the actives and corresponding controls diluted in a culture medium are added. At the end of a five-day incubation period, the supernatant is removed, the cells are washed with PBS and fixed. The cells are then incubated with the primary Fibrillin 1 monoclonal antibody (11C1.3) (Thermo Fisher) diluted in blocking buffer at a concentration of 1:200. The cells are incubated. The primary antibody is removed, and the cells are washed with PBS. The secondary antibody was added at a dilution of 1:1000 in blocking buffer, then removed and the cells are washed with PBS. The formation of Fibrillin 1 by the cells is visualized using a fluorescence microscope. The obtained images are analyzed using an image processing software assigning a numerical value to the coverage density.

Results

TABLE 2

| | Pal-LLAN-OH (8 ppm) (SEQ ID NO: 7) |
| --- | --- |
| Fibrillin 1 (significance) | +108% (p < 0.05) |

All these results show the interest of the tetrapeptide according to the invention for a cosmetic treatment based in particular on the stimulation of the synthesis of collagen I and Fibrillin 1 by the fibroblasts of the ECM and at concentrations of a few ppm.

2—Stimulation of Hair Growth 2.1—Proliferation Studies on Cell Cultures (Hair Follicle Dermal Papilla Cells (HFDPC) and Outer Root Sheath Keratinocytes (ORSK))

Protocol

The cells are seeded in adapted culture media and incubated for 24 h. Then the culture media are removed and changed for test media and cells are incubated. The cells are thereafter contacted with the peptide (diluted at different concentrations in DMSO) and with EdU (Ethynyldeoxyuridine), a thymidine-analogue nucleoside which is incorporate into the newly synthetized in proliferating cells. The cultures are stopped, and cells are labelled using a Edu detection kit.

Results

TABLE 3

| | HFDPC | |
| --- | --- | --- |
| Pal-LLAN-OH (SEQ ID NO: 7) | Cell proliferation variation % vs. control solvent (DMSO) | Significance vs. control |
| 5 ppm | +13.7% | p < 0.01 |
| 10 ppm | +22.15% | p < 0.01 |

These results show that the peptide of the invention induces a significant proliferation of HFDPC after contact with the peptide according to the invention.

TABLE 4

| | ORSK | |
| --- | --- | --- |
| Pal-LLAN-OH (SEQ ID NO: 7) | Cell proliferation variation % vs. control solvent (DMSO) | Significance vs. control |
| 5 ppm | +55% | p < 0.01 |

These results show that the peptide of the invention induces a significant proliferation of ORSK after contact with the peptide according to the invention.

2.2—Hair Growth from Hair Follicle Bulbs

Protocol

Hair Preparation:

Whole follicles (including the infundibulum, upper sheath, bulge, lower sheath, and bulb) are isolated by microdissection from scalp explants issued from surgery. On first day (DO), the hairs are placed individually in wells and keep alive at 37° C. in a humid atmosphere, enriched with 5% $CO_2$, in an adapted culture medium.

Preparation of the Peptide Products for the Treatments:

Peptide solutions at 10 ppm and 5 ppm are prepared in the culture medium with 0.1% DMSO.

Treatments:

On D0, D3, D5 and D7, the peptide products are incorporated into the culture medium. The culture media are completely renewed for each treatment. The control cases receive no treatment other than renewal of the culture medium.

Specimens:

On day D0, the hairs are removed and stored frozen at −80° C. On D10, the hairs from each case are taken and treated in the same way.

Growth Measure:

A photograph of the isolated hairs is taken on DO to measure the hair from the bulb to the end of the hair shaft using an image analysis software. The photographs and length measurements are repeated on D3, D5, D7 and D10. The growth of each hair is monitored individually.

Results

During the study, the hairs grow. To estimate the effect of the peptide, the average hair length between the peptide and the solvent control are compared, for each time (see below Table 5).

TABLE 5

| Growth variation compared to solvent control (0.1% DMSO) for each time | | | | |
| --- | --- | --- | --- | --- |
| Pal-LLAN-OH (SEQ ID NO: 7) | D3 | D5 | D7 | D10 |
| 5 ppm | +21% (nsd) | +26%* | +32%** | +30%** |
| 10 ppm | +16% (nsd) | +28%* | +37% | +38% | nsd: non significant data;
*p < 0.05;
**p < 0.01

These results show a significant stimulation of hair growth from D5 until D10 (study stop time).

D—Galenics

Different formulations are described below. Additional cosmetic active ingredients, supporting and/or supplementing the activity of the active ingredient according to the invention, can be added in the appropriate phase depending on their hydrophobic or hydrophilic nature. These ingredients can be of any category according to their role(s), the place of application (body, face, neck, bust, hands, hair, eyelashes, eyebrows, body hair, etc.), the desired final effect and the targeted consumer, for example antioxidant, hydrating, nourishing, protective, smoothing, remodeling, volumizing (lipofilling), acting on complexion radiance, treating spots, concealer, anti-glycation, slimming, soothing, myorelaxing, anti-redness, anti-stretch marks, etc. Examples are mentioned above in the description.

The formulas described below include an active ingredient based on a tetrapeptide according to the invention as described in point B above, comprising 1200 ppm of tetrapeptide. The formulas could also contain a mixture of these two tetrapeptides according to the invention formulated from an active ingredient comprising them in equal proportions or not. These formulas are given as a guide and may contain higher percentages of the active ingredient according to the invention.

1) Cream Form, for Example for an Anti-Aging Day or Night Cream for the Face

TABLE 6

| Raw material | INCI name | Role | % |
| --- | --- | --- | --- |
| Part A: | | | |
| H₂O | / | / | qsp 100 |
| CARBOPOL ™ Ultrez 10 | Carbomer | Thickener/Gelling agent | 0.30 |
| Part B: | | | |
| BRIJ ™ S2-SS-(RB) | Steareth-2 | Emulsifier | 0.40 |
| BRIJ ™ S10-SO-(RB) | Steareth-10 | Emulsifier | 1.20 |
| CRODAFOS ™ CES-PA-(RB) | Cetearyl Alcohol (and) Dicetyl Phosphate (and) Ceteth-10 Phosphate | Emulsifier/conditionner | 4.00 |
| CRODACOL ™ CS90-PA-(RB) | Cetearyl Alcohol | Emollient | 1.50 |
| Laurocapram | Laurocapram | Emollient | 2.50 |
| CRODAMOL ™ AB-LQ-(RB) | C12-15 Alkyl Benzoate | Emollient | 1.50 |
| CRODAMOL ™ OSU-LQ-(JP) | Diethylhexyl Succinate | Emollient | 7.00 |
| Part C: | | | |
| Glycerin | Glycerin | Humectant | 2.50 |
| Octanediol | Caprylyl Glycol | Humectant/Emollient | 0.50 |
| Part D: | | | |
| Phenoxyethanol | Phenoxyethanol | Preservative | qs |
| Part E: | | | |
| Potassium sorbate | Potassium Sorbate | Preservative | qs |
| Part F: | | | |
| H₂O | / | / | 4.00 |
| NaOH 30% | Sodium Hydroxide | pH adjuster | 0.40 |
| Part G: | | | |
| Ingredient comprising the tetrapeptide(s) according to the invention | / | Active | 3.00 |

Examples of Additional Active Ingredients:

Supplementing the Activity:

1—an ingredient acting on the skin elastic properties, such as:

IDEALIFT™, marketed by Sederma, comprising the N-acetyl-Tyrosyl-Arginyl-O-hexadecyl ester lipopeptide, fighting against facial flaccidity and improving gravity resistance through elastin stimulation.

BPEL™, marketed by Sederma, comprising the Pal-VGVAPG (SEQ ID NO: 3) peptide.

2—an ingredient actif more specifically on epiderm, such as:

CRYSTALIDE™, marketed by Sederma, comprising the Pal-KTFK (SEQ ID NO: 22) peptide, vectorised in the epiderm thanks to a oil-wax-surfactants and water microemulsion in which the peptide is solvated, exerting a bio-harmonic action in the epidermis by regulating epigenetic and inflammatory phenomena, and by harmonizing the process of skin maturation.

3—a moisturizing/smoothing ingredient, such as:

OPTIMHYAL™, marketed by Sederma, contains oligosaccharides of acetylated glucuronic acids having a structure similar to fragments of hyaluronic acid.

4—a sebum-regulating ingredient, such as:

SEBULESS™, marketed by Sederma, comprising a *Syringa vulgaris* extract produced by in vitro plant cell culture, which is a purifying sebum regulator, that mattifies and refreshes the complexion, and blurs imperfections.

5—an ingredient acting on the harmful effects of blue light, such as:

SYNCHROLIFE™, marketed by Sederma, comprising the Pal-GQPR peptide (SEQ ID NO: 2), chrysin and a rosemary extract; rebalances the production of key molecules of the circadian cycle (opsin5, period2, melatonin) and ensures a reinforced repairing metabolism (energy, antioxidant, anti-inflammatory and repair of the skin matrix).

Reinforcing the activity: an ingredient acting on the synthesis of ECM macromolecules, such as: MATRIXYL® (based on the Pal-KTTKS (SEQ ID NO: 1) peptide, MATRIXYL® 3000 (based on a mixture of the Pal-GQPR (SEQ ID NO: 2) and Pal-GHK peptides), MATRIXYL® SYNTHE'6® (based on the $KM_2K$ peptide) and/or MATRIXYL® MORPHOMICS® (based on the Pal-K(P) HG peptides), that are marketed by Sederma.

PORETECT™, marketed by Sederma, comprising a combination of flax and celery seed extracts titrated in cylolinopeptides and senkyunolides, which brings firmness, tone and density to the skin, thus reinforcing the maintaining structures of skin pores which sag with the age.

FEMRAGE™ marketed by Sederma, comprising an *Engelhardia chrysolepis* extract titrated in astilbin, a glycosylated flavonoid, offering elastic and firming properties to the skin, particularly in postmenopausal women.

2) Aqueous Mild Serum Form

TABLE 7

| Raw material | INCI name | Role | % |
| --- | --- | --- | --- |
| Part A: | | | |
| $H_2O$ | / | / | qsp100 |
| Potassium sorbate | Potassium Sorbate | Preservative | 0.10 |
| Part B: | | | |
| Glycerin | Glycerin | Humectant | 5.00 |
| Phenoxyethanol | Phenoxyethanol | Preservative | 0.80 |
| Part C: | | | |
| CROMOLLIENT™ SCE | Di-PPG-2 Myreth-10 Adipate | Emollient | 1.20 |
| VISIAOPTIMA™ SE | Sodium Polyacrylate (and) Ethylhexyl Cocoate (and) PPG-3 Benzyl Ether Myrisate (and) Polysorbate 20 | Rheology modifier and emulsion stabilizer | 1.00 |
| Part D: | | | |
| $H_2O$ | / | / | 0.80 |
| NaOH 30% | Sodium Hydroxide | pH adjuster | 0.08 |
| Part C: | | | |
| Ingredient comprising the tetrapeptide(s) according to the invention | / | Active | 3.00 |

Examples of Additional Active Ingredients, Supplementing the Activity:

1—an anti-aging ingredient, such as:

SENESTEM™, marketed by Sederma, comprising *Plantago lanceolata* plant cells obtained by in-vitro cell culture, improving the viscoelastic properties of the skin and lightening the senescence pigmentary spots.

2—an antioxidant ingredient, such as:

MAJESTEM™, marketed by Sederma, based on *Leontopodium alpinum* plant cells titrated in leontopodic acid, obtained by in-vitro cell culture, neutralizing oxidative stress (pollution, UVB radiation) and restoring cutaneious tense.

3) Gel Form

TABLE 8

| Raw material | INCI name | Role | % |
|---|---|---|---|
| Part A: | | | |
| H₂O | / | / | qsp100 |
| Carbomer | / | Rheology modifier | 0.40 |
| Part B: | | | |
| Glycerin | Glycerin | Humectant | 7.00 |
| Phenoxyethanol | Phenoxyethanol | Conservateur | 0.80 |
| Part C: | | | |
| H₂O | / | / | 3.00 |
| NaOH 30% | Sodium Hydroxide | pH adjuster | 0.30 |

TABLE 8-continued

| Raw material | INCI name | Role | % |
|---|---|---|---|
| Part D: | | | |
| TWEEN ™ 20 | Polysorbate 20 | Emulsifier | 0.50 |
| CROMOLLIENT ™ SCE | Di-PPG-2 Myreth-10 Adipate | Emollient | 1.00 |
| COVI-OX ™ | Tocopherol (and) Helianthus Annuus (Sunflower) Seed Oil | Antioxidant | 0.40 |
| Part E: | | | |
| Ingredient comprising the tetrapeptide(s) according to the invention | / | Active | 3.00 |

Examples of Additional Active Ingredients, Supplementing the Activity:

1—an antipollution ingredient, such as:

CITYSTEM™, marketed by Sederma, based on *Marrubium vulgare* plant cell having a high Forsythoside B concentration, produced by in-vitro plant cell culture, used against pollution attacks, makes the skin soft and smooth, refines skin texture, reduces blackhead visibility, leaving the skin radiant and purified.

2—a calming ingredient for sensitive skin, such as:

PACIFEEL™, marketed by Sederma, comprising a *Mirabilis jalapa* plant extract.

3—a moisturizing ingredient such as:

AQUALANCE™, marketed by Sederma, an osmoprotective moisturizer composed of homarin and erytlyritol.

4) Gel Form to Make a Spray Mask

TABLE 9

| Raw material | INCI name | Role | % |
|---|---|---|---|
| Part A: | | | |
| H₂O | / | / | qsp100 |
| HYDROTRITICUM ™ PVP PE | Aqua (and) Hydrolyzed Wheat Protein/PCP Crosspolymer | Filmogen agent | 3.00 |
| VOLAREST ™ FL | Acrylates/Beheneth-25 Methacrylate Copolymer | Rheology modifier | 2.30 |
| Potassium sorbate | Potassium Sorbate | Preservative | |
| Part B: | | | |
| Glycerin | Glycerin | Humectant | 5.00 |
| Phenoxyethanol | Phenoxyethanol | Preservative | 0.80 |
| Part C: | | | |
| CROVOL ™ A70 | PEG-60 Almond Glycerides | Emollient | 1.00 |
| Ethanol | Ethanol | Solvent | 5.00 |
| COVI-OX ™ | Tocopherol (and) Helianthus Annuus (Sunflower) Seed Oil | Antioxidant | 0.20 |
| Part D: | | | |
| H₂O | / | / | 2.50 |
| NaOH 30% | Sodium Hydroxide | pH adjuster | 0.25 |
| Part E: | | | |
| Ingredient comprising the tetrapeptide(s) according to the invention | | Active | 3.00 |

Examples of Additional Active Ingredients, Supplementing the Activity:

1—an ingredient acting on complexion radiance, such as:

EVERAT™ marketed by Sederma, comprising a combination of an *Enantia chlorantha* extract rich in protobberberins and oleanolic acid, decreasing pore size and shine, refining acne-prone skin texture.

2—an ingredient with revitalizing properties, such as:

Fruitliquid™ Kumquat™, marketed by Crodarom.

5) Cream Form, for a Make-Up Base

TABLE 10

| Raw material | INCI name | Role | % |
|---|---|---|---|
| Part A: | | | |
| H₂O | / | / | qsp 100 |
| VOLAREST ™ FL | Acrylates/Beheneth-25 Methacrylate Copolymer | Rheology emulsifier | 0.90 |
| Part B: | | | |
| ARLACEL ™ 2121 | Sorbitan Stearate (and) Sucrose Cocoate) | Emulsifier | 4.50 |
| Part C: | | | |
| Pentylene glycol | Pentylene Glycol | Humectant | 5.00 |
| Phenoxyethanol | Phenoxyethanol | Conservateur | 0.80 |
| Part D: | | | |
| CRODAMOL ™ SSA | Decyl Isostearate (and) Isostearyl Isostearate | Emollient | 2.00 |
| CRODAMOL ™ TN | Isotridecyl Isononanoate | Emollient | 2.00 |
| CRODAMOL ™ AB | C12-C15 Alkyl Benzoate | Emollient | 1.50 |
| CRODAMOL ™ GTEH | Triethylhexanoin | Emollient | 3.00 |
| COVI-OX ™ | Tocopherol (and) Helianthus Annuus (Sunflower) Seed Oil | Antioxidant | 0.10 |
| Part D: | | | |
| Potassium sorbate | Potassium Sorbate | Preservative | 0.10 |

TABLE 10-continued

| Raw material | INCI name | Role | % |
|---|---|---|---|
| Part E: | | | |
| H₂O | / | / | 2.50 |
| NaOH 30% | Sodium Hydroxide | pH adjuster | 0.25 |
| Part E: | | | |
| Ingredient comprising the tetrapeptide(s) according to the invention | | Active | 3.00 |

Examples of Additional Active Ingredients, Supplementing the Activity:

1—an ingredient for treating eye dark circles and contour, such as:

HALOXYL™, marketed by Sederma, an association of two matrikins, the Pal-GHK and the Pal-GQPR (SEQ ID NO: 2) with N-hydroxysuccinimide and a flavonoid, chrysin.

EYELISS™, marketed by Sederma, combining three components methyl chalcone hesperidin, the Valyl-Tryptophan peptide (VW) and the Pal-GQPR (SEQ ID NO: 2) lipopeptide.

PRODIZIA™, marketed by Sederma, comprising an *Albizia julibrissin* plant extract, favorising the reduction of visible of fatigue: dark circles, under eyes bags, dull complexion and drawn features by repairing and protecting skin from damages caused by glycation.

2—anti-wrinkles/anti-aging ingredient comprising peptide(s) such as: MATRIXYL® 3000 MATRIXYL® SYNTHE'6® and/or MATRIXYL® MORPHOMICS® marketed by Sederma.

3—an ingredient acting on skin radiance such as AMBERSTEM™, marketed by Sederma, which embellishes olive carnation skins, derived from the cell culture of Buddleja *davidii* leaves (butterfly tree), acting on skin radiance by reducing inflammatory hyperpigmentation, dull complexion and redness while strengthening skin barrier and hydration.

The invention claimed is:

1. A tetrapeptide of Formula 1:

X-LLAN-Z        (SEQ ID NO: 6, Formula 1), wherein:

X is selected from H, —CO—$R^1$, —$SO_2$—$R^1$ or a bioti-noyl group;

Z is selected from OH, $OR^1$, $NH_2$, $NHR^1$ or $NR^1R^2$; and $R^1$ and $R^2$ are independently selected from alkyl, aryl, aralkyl, alkylaryl, alkoxy, saccharide, or aryloxy group, wherein the group is linear, branched, cyclic, polycy-clic, unsaturated, hydroxylated, carbonylated, and/or phosphorylated, wherein the group has no more than 24 carbon atoms, and wherein the group optionally com-prises one or more heteroatoms selected from O, S and/or N in its backbone.

2. The tetrapeptide according to claim 1, wherein $R^1$ and $R^2$ independently have at least 3 carbon atoms.

3. The tetrapeptide according to claim 1, wherein X is —CO—$R^1$, and Z is a group selected from OH, OMe, OEt or $NH_2$.

4. The tetrapeptide according to claim 1, wherein the —CO—$R^1$ group is selected from octanoyl (C8), decanoyl (C10), lauroyl (C12), myristoyl (C14), palmitoyl (C16), stearoyl (C18), elaidoyl, oleoyl or lipoyl.

5. The tetrapeptide according to claim 1, wherein Z is OH.

6. The tetrapeptide according to claim 5, wherein the peptide is Pal-LLAN-OH (SEQ ID NO: 7).

7. A cosmetic composition comprising at least one tetra-peptide according to claim 1 and a physiologically accept-able medium.

8. The composition according to claim 7, wherein the amount of the tetrapeptide is between 10-7% (w/w) and 20% (w/w) relative to the total weight of the composition.

9. The composition according to 7, wherein the compo-sition further comprises at least one additional active ingre-dient selected from the group consisting of vitamin B3, niacinamide, tocopherol, retinoid compounds, hexamidine, α-lipoic acid, resveratrol, dehydroepiandrosterone (DHEA), hyaluronic acid and one or more cosmetic peptides.

10. The composition according to claim 7, wherein the composition further comprises a mixture of Pal-GHK and Pal-GQPR (SEQ ID NO: 2), and/or the peptide Ac-YR-hexadecyl ester.

11. A method of improving general condition of skin and/or hair in a subject, wherein the method comprises applying at least one tetrapeptide according to claim 1 to the skin and/or the hair of the subject.

12. The method according to claim 11, wherein the tetrapeptide is applied topically.

13. The method according to claim 11, wherein the method is for anti-aging treatment.

14. The method according to claim 11, wherein the method is for one or more of:

treating wrinkles and fine lines;

improving firmness, tone, elasticity, and/or flexibility of the skin;

increasing the density and volume of the skin;

treating stretch marks;

treating skin sagging; and/or improving the uniformity and radiance of the skin com-plexion.

15. The method according to claim 11, wherein the method is for treating hair.

16. The method according to claim 15, wherein the method is for stimulating hair growth.

* * * * *